US00PP34828P2

(12) United States Plant Patent
Adams et al.

(10) Patent No.: US PP34,828 P2
(45) Date of Patent: Dec. 13, 2022

(54) HEMP PLANT NAMED '3 CROP'

(50) Latin Name: ***Cannabis* spp.**
Varietal Denomination: 3 Crop

(71) Applicant: GeneticsCubed, LLC, Hurricane, UT (US)

(72) Inventors: Arthur Adams, Santa Clara, CA (US); Thomas Azwell, Berkeley, CA (US)

( * ) Notice: Subject to any disclaimer, the term of this patent is extended or adjusted under 35 U.S.C. 154(b) by 0 days.

(21) Appl. No.: 17/481,046

(22) Filed: Sep. 21, 2021

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258
See application file for complete search history.

*Primary Examiner* — Karen M Redden
(74) *Attorney, Agent, or Firm* — David R. Conklin; Kirton McConkie

(57) ABSTRACT

The present invention provides a new and distinct variety of hemp designated as '3 Crop', wherein '3 Crop' comprises improved resilience to high salinity soil.

5 Drawing Sheets

Latin name of the genus and species of the plant claimed: *Cannabis* spp.

Variety denomination: '3 Crop'.

BACKGROUND OF THE INVENTION

*Cannabis* is the genus of a variety of species—*Cannabis sativa, Cannabis ruderalis*, and *Cannabis indica*—which is often used as an umbrella term to refer to them all. This misclassification of the different species has made it difficult to properly distinguish between and understand the best ways to utilize the different varieties of these plants.

According to the 2018 Farm Bill, Hemp is a variety of *Cannabis sativa* that is distinguished by its low tetrahydrocannabinol (THC) levels of less than 0.3%. THC is the only currently known psychoactive compound found in *Cannabis*, however there are many additional cannabinoid compounds that can be utilized in a variety of ways. The exact concentration results based on lab testing of dried flowers will vary depending on growing conditions of the plant, and sampling, preparation, and testing methods used. THC production, for example, is a natural defense mechanism for the plant, meaning in high stress or threatening environments the specific plant will produce higher levels of THC. Because of this inconsistency, many state labs are allowing slightly higher levels of THC in the tests as anything under 1% THC has not been proven to have psychoactive effects.

For the purpose of this study on '3 Crop', the cannabinoid percentages are recorded based on a plant grown in a high-stress environment to determine the maximum concentration of THC that will be produced by this specific strain. The results conclude that the '3 Crop' is a type-III hemp cultivar meaning it does not possess the allele to ever make more than 0.5% THC (and thus is not suitable for marijuana use). Additionally, '3 Crop' is a new, unique variety because of its potential to be utilized as a tricrop, meaning its stalks can be used to create fiber. As a mother it produces many strong, viable seeds and maintains elevated cannabinoid levels.

Before medicinal hemp and cannabidiol (CBD) became popularized, industrial hemp was prominently grown for fiber to make paper, fabric, rope, or other materials. The stalks were the part of the plant that were needed for fiber, so there wasn't a focus on the flower or increasing cannabinoid levels. At the time that industrial hemp was prominent, the abundance of cannabinoids were produced in marijuana cultivars which were criminalized due to the presence of the psychoactive cannabinoid, THC. With the recent discovery of the medicinal properties of other cannabinoids, such as CBD, cannabichromene (CBC), and cannabigerol (CBG), the hemp industry shifted towards a hybrid of the industrial hemp with marijuana to isolate plants with high levels of CBD but low levels of THC. This shift in the market made it so hemp was grown to produce large, robust flowers with high cannabinoid concentration instead of stalks for fiber.

The industry shift to cannabinoids also pulled the focus away from the other beneficial qualities of hemp, including its nutritious seeds. Not only do the seeds have a significant amount of nutrients and protein, but they can be pressed for oil that can be used to produce paints, soaps, and even biofuel. As CBD floods the market, it will become more apparent that the best way to have success with growing hemp is to not focus exclusively on the flowers and cannabinoids, but rather look at the other aspects of the plant. For a farmer to select three different strains that each have one of the qualities listed above, it will be more effort to manage three different crops and the different maintenance and supplements needed for them to individually thrive. A tricrop cultivar will allow farmers to have all three things without having to adjust for different strains. It grows dense, aromatic flowers with vast cannabinoid concentrations and terpene profiles on tall, thick stalks with large, fibrous internodes. When allowed to fertilize, the stalks are sturdy enough to hold up the flowers that are heavy with large yields of seeds without breaking. Additionally, the seeds harden and reach maturity after one month post-pollination which is much faster than other plants that often take two months to develop fully matured and hardened seeds.

'3 Crop' is a new and distinct variety of hemp plant exhibiting a CBD:CBG:THC ratio of 22:2:1, and improved resilience to high salinity soils. '3 Crop' was developed in a selective breeding program by performing controlled fertilization of known, high-performing hemp varieties. The purpose of the research was to determine which cultivars would not only produce high levels of CBD while maintaining the legal limit of THC, but also could be used to produce fiber and seeds. The research also was striving to isolate varieties of plants with high concentrations of novel cannabinoids that have not been isolated in mass. The father, W, was selected because of its characteristically high levels of CBG at maturity and was crossed with 27 different females to determine which would pass the CBG trait. One hundred of each of the newly produced seeds were germinated and grown indoors to identify the best new phenotype. Of them, many had the potential to be a tricrop and used for fiber and seed in addition to cannabinoids. '3 Crop' was the best-performing individual selected from nearly 3,000 plants due to its vigor, large yield of large seed, large stalks with fibrous qualities, high cannabinoid content and unique terpene profile.

BRIEF SUMMARY OF THE INVENTION

This invention relates to a new and distinctive hemp cultivar designated as '3 Crop'.

As used herein, the term "cultivar" is used interchangeably with the terms "variety," strain," and/or "clone."

Progenies have been reproduced asexually via apical stem cuttings from vegetative plants. Additionally, '3 Crop' has a stable seed line.

BRIEF DESCRIPTION OF THE DRAWINGS

The accompanying photographs illustrate the new hemp variety.

DETAILED BOTANICAL DESCRIPTION

Figure 1:
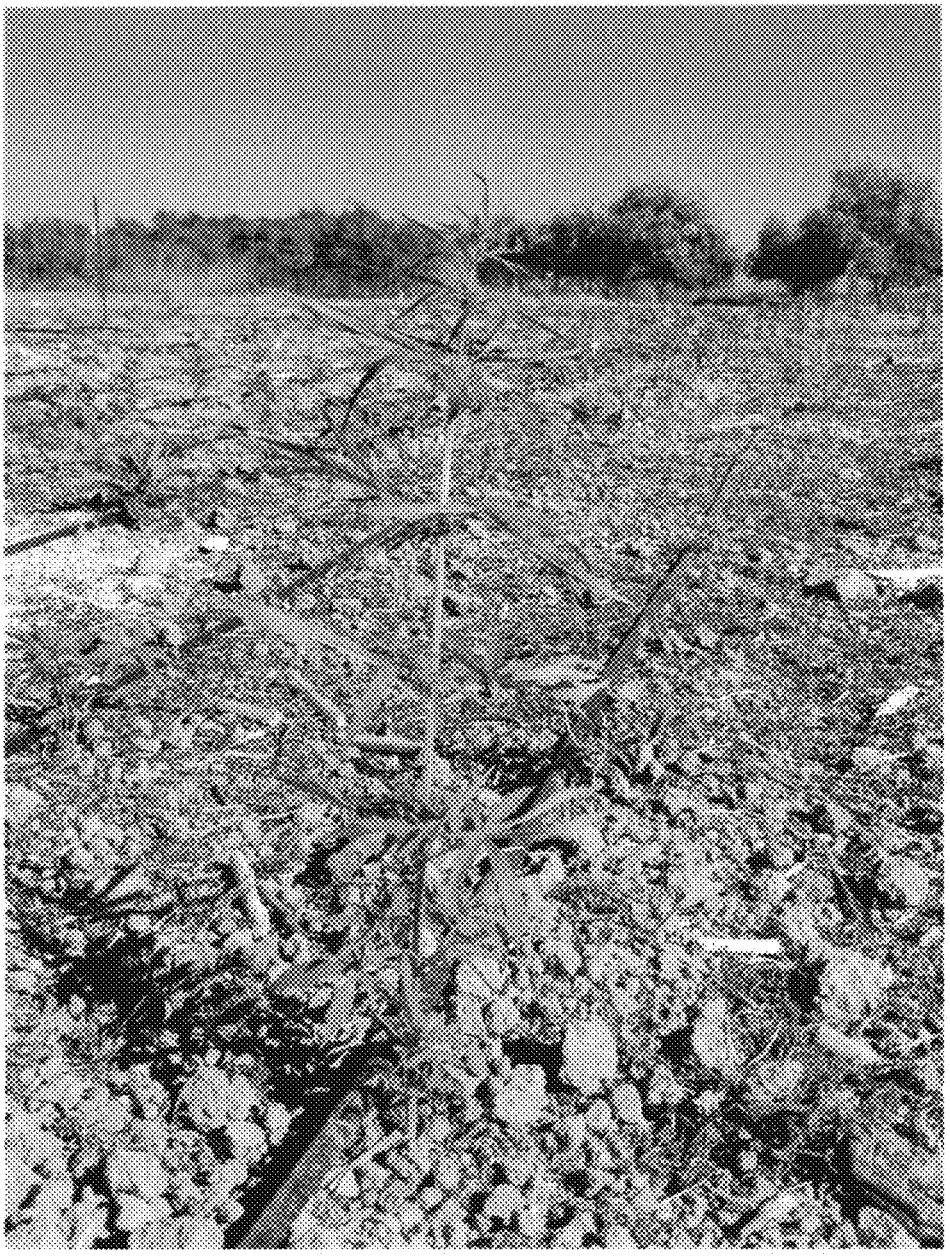
FIG. 1 shows a perspective view of '3 Crop' grown from seed outdoors in high salinity soil. Notice the significant vegetative growth and long stalks compared to surrounding strains.
Figure 2:
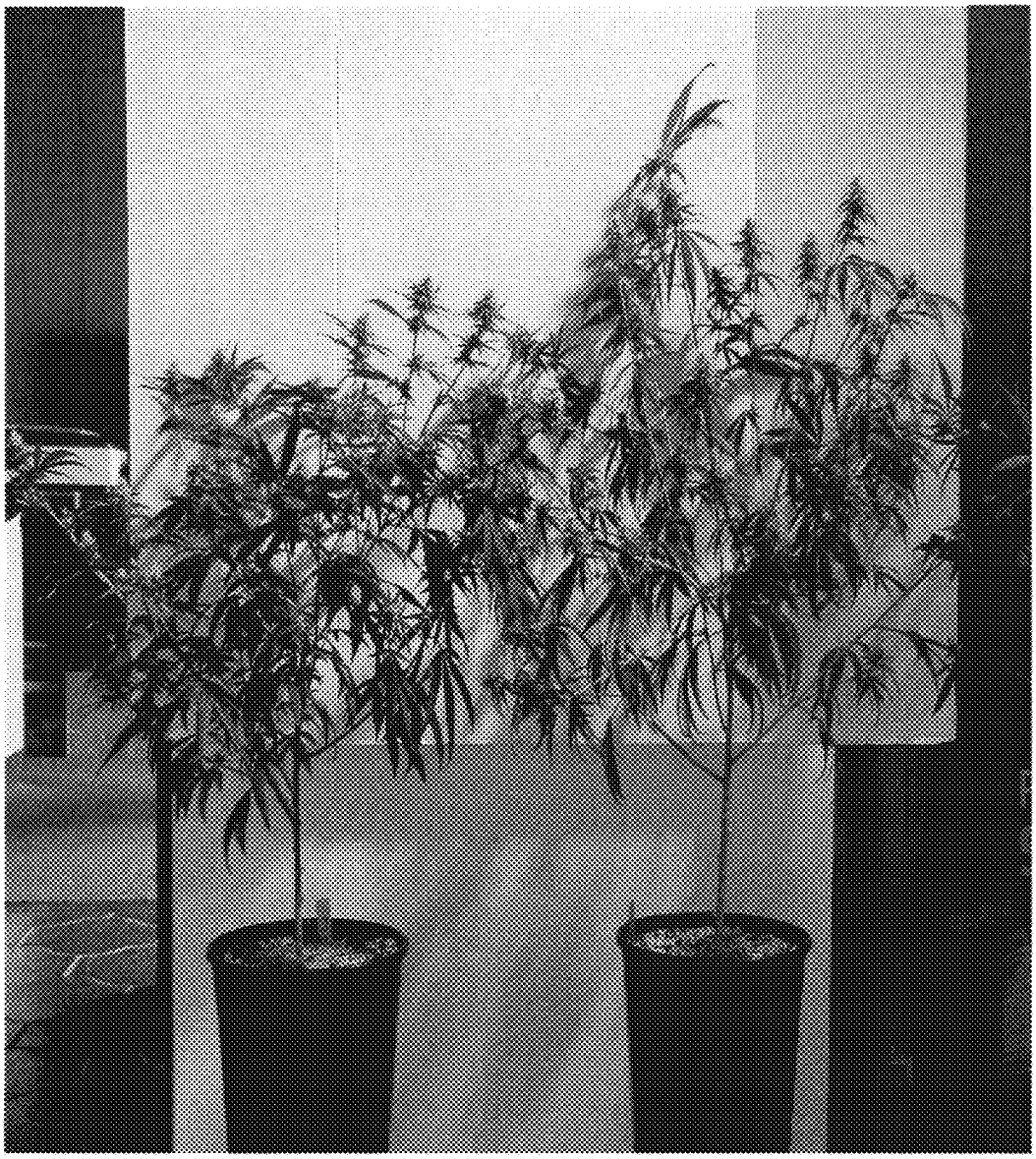
FIG. 2 shows a perspective view of '3 Crop' (left) next to U mother (right) both grown from clones and transplanted at the same time. The photo was taken 4 weeks after flowering was induced in the plants. Notice '3 Crop' is taller with larger internodes, but has similar leaf structures to the mother. Both were topped in the vegetative stage to induce branching which limited the vertical growth possible by '3 Crop'.
Figure 3:
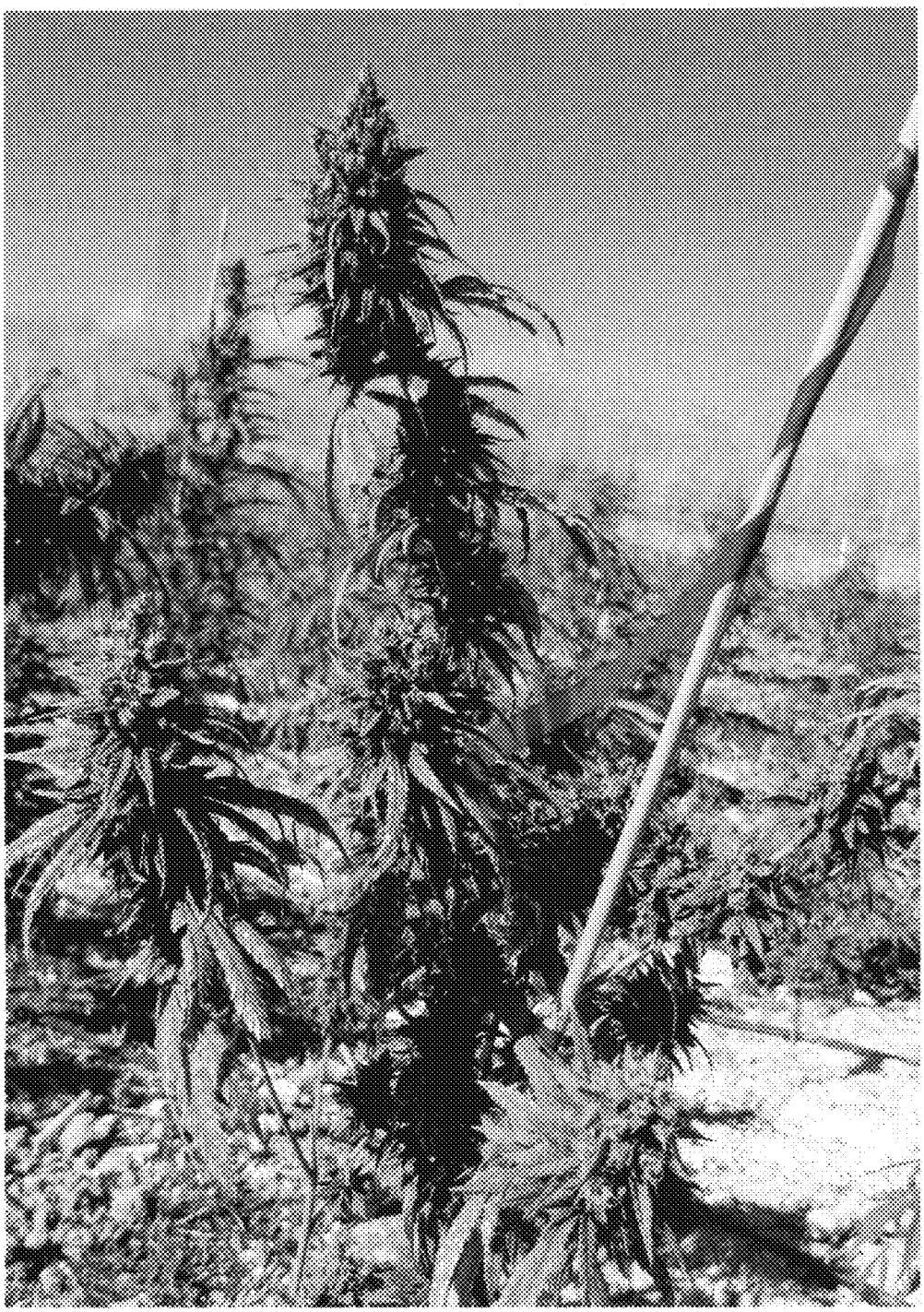
FIG. 3 shows a perspective view of '3 Crop' grown outdoors from clone after vegetative growth was confined to a small pot causing the plant to be root bound. This photo doesn't exhibit the fibrous stalks because the vegetative state was stunted, however, it shows the dense, thick flower that '3 Crop' is capable of producing.
Figure 4:
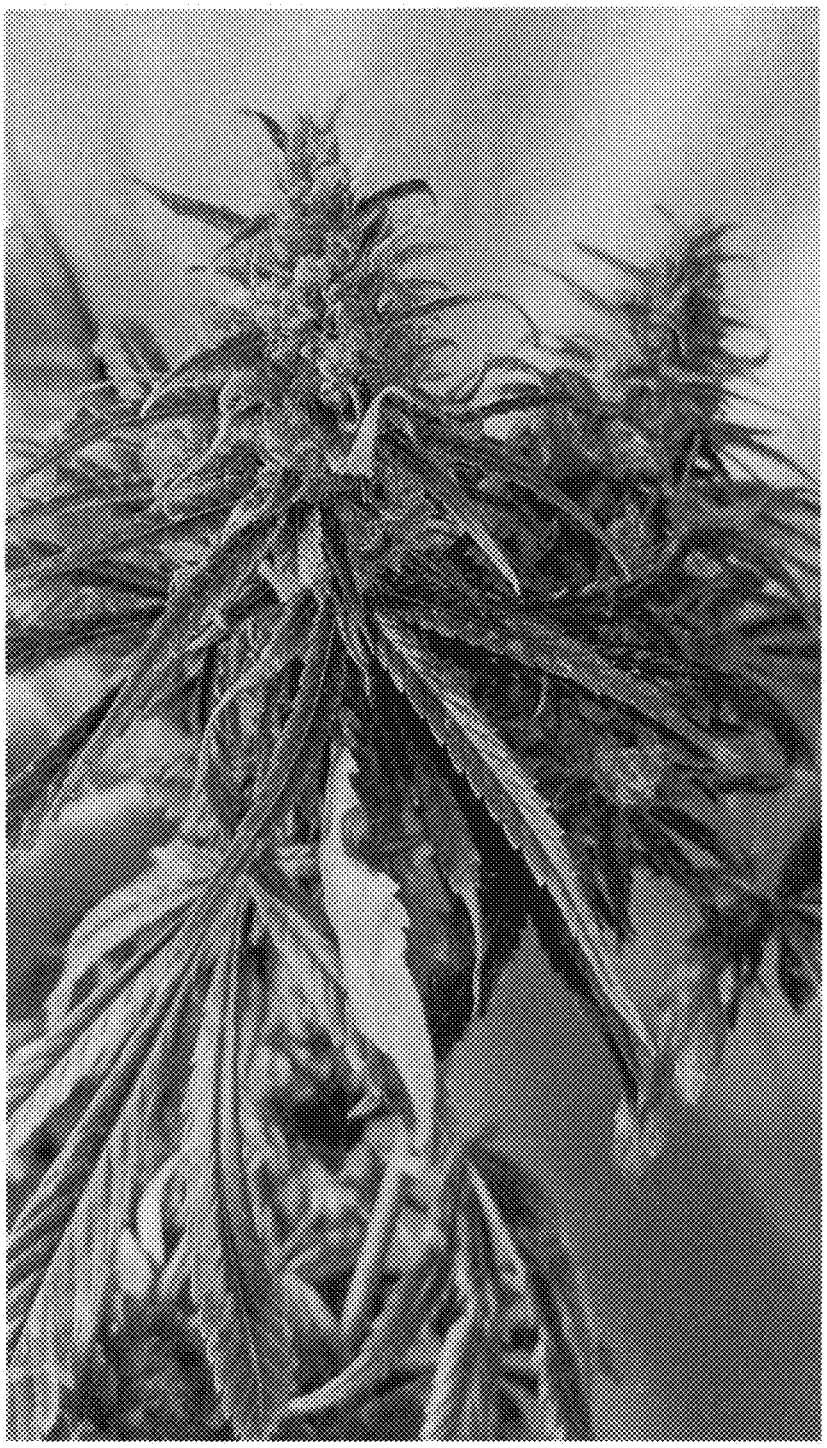
FIG. 4 shows a perspective view of a top flower of pregnant '3 Crop' grown indoors taken one week before harvest. Seeds matured approximately one month faster, compared to other plants that take two months post-pollination to fully mature.
Figure 5:
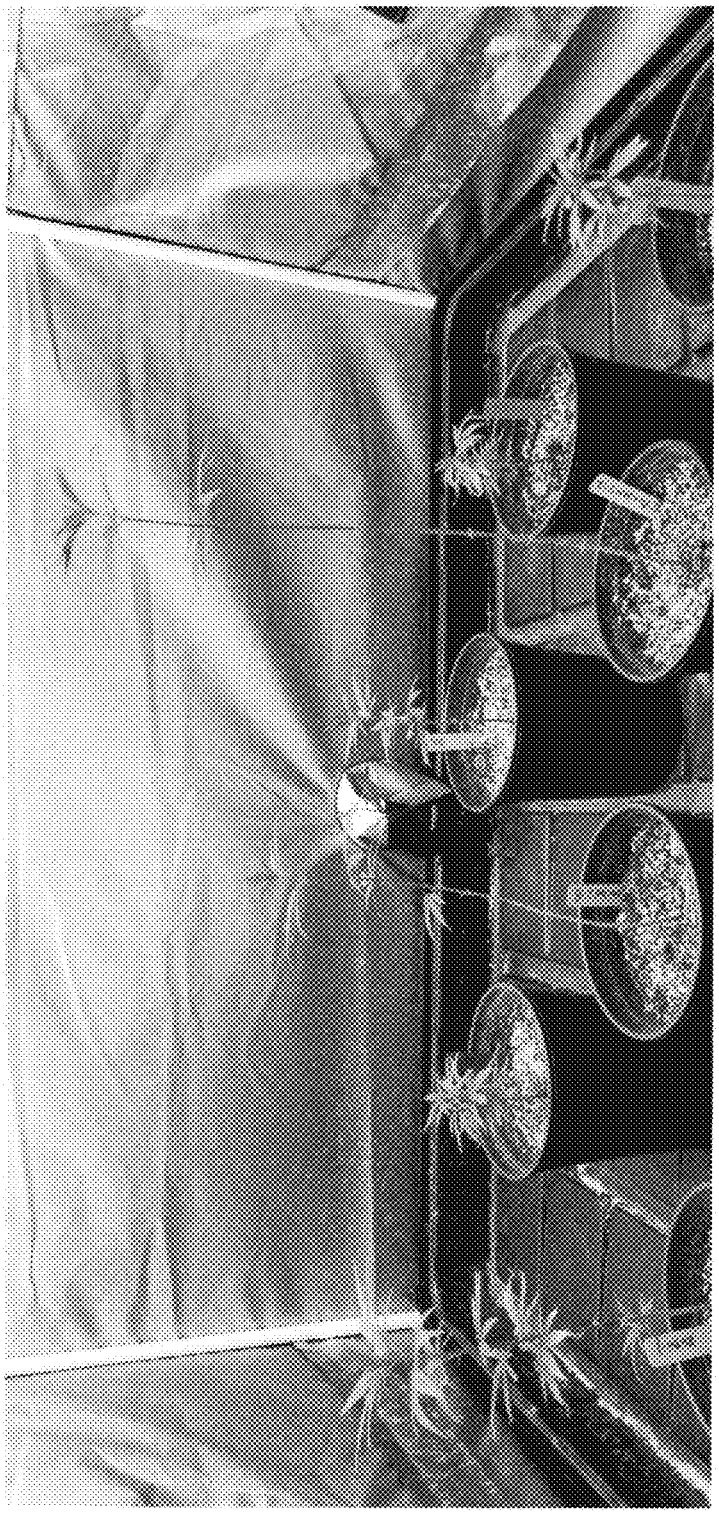
FIG. 5 shows a perspective view of clones taken from 6 different genotypes and allowed to root and grow for one month in rockwool before planting in soil. The middle two plants are 2 phenotypes (sisters) of '3 Crop' and exhibit their intense vegetative growth as seen by the large stalk and wide internodes as compared to surrounding strains that have remained shorter and focus more on leaf development than growth of a sturdy, fibrous stalk.

'3 Crop' has been examined in manipulated conditions grown indoors. The variety has not been grown in all possible conditions, thus different environmental factors alter the appearance or composition of this phenotype. The individual has been reproduced asexually via apical stem cuttings from vegetative plants in Sonoma County, Calif. Additionally, '3 Crop' has a stable seed line.

In the following description, the color determination is in accordance with The Royal Horticultural Society Colour Charts, Fifth Edition (referred to herein as "R.H.S.", available at rhscf.orgfree.com, last visited Aug. 25, 2020) except where general color terms of ordinary dictionary significance are used. Note that variation in color for the same plant on the leaves and stalks can be a result of different nutrient formulas and different amounts of watering. Coloration should only be used as a general picture rather than the distinguishing features.

TABLE 1

| General | | |
|---|---|---|
| Characteristics | New Variety '3 Crop' | Parental Variety (U) (Female Plant) |
| Plant Life Form | Herbaceous plant (herb) | Herbaceous plant (herb) |
| Plant Growth Habit | Upright, monoecious, annual, averaging 80% Female and 20% hermaphrodite with the hermaphrodite averaging 90% Female Flowers and 10% Male Flowers | Upright, dioecious, annual, no hermaphrodite or monoecious tendencies without stress conditions |
| Plant origin | '3 Crop' was created in a selective breeding program from a cross between the Mother, U, hemp variety and the Father, W, hemp variety. | Origin unknown |
| Plant Propagation | Asexually reproduced via apical stem cutting and cloning from mother in vegetative state | Asexually reproduced via apical stem cutting and cloning from mother in vegetative state |
| Propagation ease | Easy | Easy |
| Propagation Condition | 80° F., 90% humidity | 80° F., 90% humidity |
| Height (unit: feet) | Outdoors may reach 10 feet at maturity<br>Indoors may reach 8 feet at maturity depending on growth conditions | Outdoors may reach 8-10 feet at maturity<br>Indoors may reach 3-4 feet depending on growth conditions |
| Width (unit: feet) | Outdoors may reach 3 feet at maturity<br>Indoors may reach 2 feet depending on growth conditions<br>This plant generally grows very tall with minimal foliage and buds. This long growth allows for stalks to be used for fibers | Outdoors may reach 6-8 feet<br>Indoors may reach 1-2 feet |
| Time to Harvest | 60 Days from Induction of flowering light cycle | 60 Days from Induction of flowering light cycle |
| Resistance to Pests or disease | Resistant to *Podosphaera macularis* (Powdery mildew), *Tetranychu surticae* (Mite), *Myzus persicae* (Green Peach Aphid), *Phorodon cannabis* (Bhang Aphid), and *Aphis fabae* (Black Bean Aphid). | More prone to *Podosphaera macularis* (Powdery mildew)<br>Has resistance to more bugs |

TABLE 1-continued

| General | | |
|---|---|---|
| Characteristics | New Variety '3 Crop' | Parental Variety (U) (Female Plant) |
| Genetically Modified Organism? | No | No |

TABLE II

| Leaf/Foliage | | |
|---|---|---|
| Characteristics | New Variety '3 Crop' | Parental Variety (U) (Female Plant) |
| Leaf Arrangement | Spiral alternate leaf arrangement with the buds growing closer together relative to the large internodes. In some locations, the branching appears more opposite than alternate. | Spiral alternate leaves and branching. |
| Leaf Shape | Palmately compound with 5-9 leaflets throughout life cycle | Palmately compound with 5-7 leaflets throughout life cycle |
| Leaf Structure | Serrated margins with long, slightly ovate, lanceolate leaflets. Apex and base are both long and aristate, both dramatically narrow and taper before reaching the ends of the leaflet. Overall the leaflets are long and more broad in the center. | Serrated margins with long lanceolate leaves slightly linear. The base is much more acuminate and the apex is almost aristate. The middle portion of the leaf remains broader for longer before narrowing again. |
| Leaf Margins | Margins are serrated with points that are almost treated from linear sides of the serration. Tips of the serration slightly point inward. | Margins are serrate with the outside of the serrations being slightly convex and the inner side of the serration being slightly concave. The tips are less angled inward than compared to the offspring. |
| Leaf Hairs | Absent | Absent |
| Leaf Length with Petiole at Maturity | 19-22 cm | 15-19 cm |
| Petiole Length at Maturity | 6-8 cm | 3-4 cm |
| Petiole Color (RHS Number) | Back side is 149C and the front has slight N79C spots | Back side is 142A and front has slight N79B color |
| Anthocyanin color and intensity in Petioles | Prominent near the node that connects the petioles to the leaflets, almost in speckled patterns and continue down, less prominently towards the stem. Also prominent in stems and stalks near the leaves or buds. | Prominent on the petiole. |
| Stipule length at maturity | 6-20 mm | 4-12 mm |
| Stipule shape | Lance shaped with acuminate/long tapering apex. Base is more broad, making a more triangular shape. | Lance shaped with tapering, acuminate apex and broad base with a less dramatic tapering. |
| Stipule Color (RHS Number) | 149C | 142A |

TABLE II-continued

| Leaf/Foliage | | |
|---|---|---|
| Characteristics | New Variety '3 Crop' | Parental Variety (U) (Female Plant) |
| Number of Leaflets | 5-9 throughout life cycle | 5-7 throughout life cycle |
| Middle Largest (longest leaflet) length | 12-14 cm | 11-14 cm |
| Middle Largest (longest leaflet) width | 2-3 cm | 2-3 cm |
| Middle Largest (longest Leaflet) length: width Ratio | 5:1 to 6:1 | 5:1 to 6:1 |
| Number of teeth of middle leaflet | 33-43 | 38-42 |
| Leaf (upper side) color (RHS Number) | 143B | N134A to 141A |
| Leaf (lower side) color (RHS Number) | 142A | 140B to 14IC |
| Leaf Glossiness | None | No glossiness, the top of the leaf is more matte |
| Vein/midrib shape | Primary veins branch out palmately with the leaflets. The 2° veins branch pinnately from the main veins and extend toward serrations with slightly convex angles upwards towards apex. 3° veins are very light and radiate out pinnately from the 2° veins particularly to connect to the indent between the serrations and additionally from the primary veins between the 2° veins. On the bottom, the 3° veins are not visible more than the protrusions. All veins make visible indentations seen from the top of the leaf. | Primary veins branch out palmately with the leaflets. The 2° veins branch pinnately from the main veins and extend toward serrations with slightly convex angles upwards towards apex. 3° veins radiate out pinnately from the 2° veins and additionally from the primary veins between the 2° veins. The 3° are most prominent, when branching from the primary veins or when branching from the 2° veins to connect to the indentation between serrations. All veins make visible indentations seen from the top of the leaf. |
| Vein/midrib color (RHS Number) | 149C | 142A |
| Aroma | Bubble gum and fruity aroma | Earthy with sweet minty undertones |

TABLE III

| Stem | | |
|---|---|---|
| Characteristics | New Variety '3 Crop' | Parental Variety (U) (Female Plant) |
| Stem Shape | At maturity, the bottom of the trunk appears to be woody and is more rounded. Father up, more prominent ridges become apparent with a | At maturity, the stalk is very sturdy and linear. Branches bend directly at the node from the stalk to point upwards |

TABLE III-continued

| Stem | | |
|---|---|---|
| Characteristics | New Variety '3 Crop' | Parental Variety (U) (Female Plant) |
| | hexagonal shape. Newer growth on branches has more prominent indentations in correlation with protrusions extending upwards from where previous branch nodes are. | then remain straight. The stems have very minimal ridges only on new growth and older growth is much smoother and more round than the off-spring. |
| Stem Diameter at Base | When grown indoors, 1-3 cm When grown outdoors, 6-13 cm | When grown indoors, 1-2.5 cm. When grown outdoors, 3-9 cm. |
| Stem Color (RHS Number) | 149A to 150A | 142A |
| Stem Pith Type | Moderate to woody | Moderate to Thick |
| Stem Internode Length | 2-9 cm | 2-9 cm |

TABLE IV

| Inflorescence | | |
|---|---|---|
| Characteristics | New Variety '3 Crop' | Parental Variety (U) (Female Plant) |
| Flowering (blooming) habit | Dioecious. | Dioecious, so grows pistillate flowers at nodes. Once branching also occurs at the node, the flower will grow above the branch before producing a flower. Flowers grow very bulbous, almost spherical. Leaves surrounding the buds radiate and are more present around apical buds. |
| Proportion of female plants | Around 50%-80% Very Stable Monoecious | 50% grown from seed, normal dioecious plant |
| Inflorescence Position | Superior with petioles of the flowers growing at an angle away from the main stalk or stem. | Superior |
| Flower arrangement | Flowers are arranged at bud sites which have larger than typical internodal spacing and will not grow together to form a cola. Individual buds are also closer and internodes are shorter near the apex of the branches. Sugar leaves radiate in spiral pattern within the flower and protrude prominently throughout the flowers. Individual calyces are clustered and overlapping to form flowers. | Flowers are much more clustered near the apex of the branch but grow relatively solitary until maturity when they are larger and overlap more prominently. The flowers radiate in a very symmetrical pattern around the branches and grow prominently above the fan leaves with minimal sugar leaves present in the actual mature buds. |
| Number of Flowers per plant | Hundreds to thousands per plant | Hundreds to thousands |
| Flower shape | The flowers grow more conically with broad bases, getting slightly wider before narrowing to the apex. Often in terminal buds there is branching of the flower creating one bud with multiple tips, almost a compound calyx of multiple flowers grouped together. | The flowers are very bulbous with multiple points of symmetry. In early flowering growth, the buds are almost spherical and become more elongated with maturity. At full maturity, the buds are significantly wider in the middle and slightly more elongated on the top than the bottom. |
| Flower (individual pistillate) length | 4-15 mm | 3-9 mm |
| Flower (compound cyme) diameter | 3-9 cm | 2-7 cm |
| Corolla | No defined corolla | No defined corolla |
| Corolla Color (RHS number) | N/A | N/A |
| Bract shape | Small, ovate with tapering apex. Difficult to locate because buds are broader and thinner so overlap on top of each other | Broad /rounded base with long, tapering apex. |
| Bract color (RHS number) | 149C | 142A |
| Bracteole shape | Same as the Bract | Same as bract |
| Bracteole color (RHS number) | 149C | 142A |
| Calyx Shape (general description) | Not Present | Not Present |
| Calyx color (RHS number) | NA | NA |
| Stigma shape | Ovate shape with long tapering apex where 2 spindle-like styles protrude. | Ovate shape with long tapering apex where 2 spindle-like styles protrude. Generally thicker and more clustered compared to the offspring |
| Stigma length | 8-21 mm | 3-7 mm |
| Stigma color (RHS number) | Newly emerged, non-fertilized stigma are milky white with slight greenish hue (128D). | 150A |
| Trichome shape | Capitate stalked gland, long stalk with smaller bulb on top. In mature plants grow on flowers, petioles, leaves and veins. | Capitate stalked gland, long stalk with smaller bulb on top. In mature plants grow on flowers and leaves. |
| Cystolithic non-glandular | On leaves farther from the bud. Leaves grow trichomes that appear glandular when surrounding the flowers. | Present on some leaves surrounding the buds. |
| Trichome color (RHS Number) | Opaque (11D), white, creamy color (19B) but changes to clear translucent to auburn (20D) and less translucent with maturity/when ready to harvest. | Opaque /white but changes with maturity/when ready to harvest. |

TABLE IV-continued

| Inflorescence | | |
|---|---|---|
| Characteristics | New Variety '3 Crop' | Parental Variety (U) (Female Plant) |
| Trichome size | 1-4 mm | 1-4 mm |
| Terminal Bud shape | When flowering: No prominent symmetry, the base of the flower is broader than the apex, creating a more conical shape. Bud branches directly from the stem with surrounding flowers much closer than axillary buds. | When flowering: Significant radial symmetry because less obstruction from nearby stem. The base of the flower is broader than the apex, but the middle is the widest creating a more ovular shape at maturity as it elongates from the initial spherical shape. |
| Terminal Bud color (RHS number) | 140B and 149C | 142A |
| Pedicle | Present in varying lengths depending on maturity and location of bud. Longer pedicles for axillary buds and shorter for buds that are closer to the apical end of branches. | Less prominent and much shorter than on the offspring. Is present closer to the main stalk, and less apparent or absent near the branch apex. |
| Pedicle length | 0.1-1.0 mm | 0.1-1.0 mm |
| Pedicle color (RHS Number) | 149A to 150A | 142A |
| Staminate shape | N/A | N/A |
| Sepal color (RHS number) | N/A | N/A |
| Pollen description | N/A | N/A |
| Seed description | Seeds are 3-4mm in length with minimal marbling throughout but no other prominent markings or lines. Seeds are dark and mature ~1 month after pollination compared to other strains that typically take ~2 months | Seeds are 2-3 mm in length. The seeds have vertical lines along the sides of the seed but only 3-4 per seed. The seed is a light brown with the vertical lines slightly more white. Some marbling occurs between or in place of the vertical lines. |
| Marbling of seed | Present but not abundant | Minimal |
| Petal description | N/A, Apetalous | N/A |

TABLE V

| Other Characteristics | | |
|---|---|---|
| Characteristics | New Variety '3 Crop' | Parental Variety (U) (Female Plant) |
| Time period and condition of flowering/blooming | Flower production is initiated when plants are taken from vegetative growth at 24-hour light and switched to 12 hours of light followed by 12 hours of dark during what would be the nocturnal period. Flowers and seeds are mature typically 75 days after flowering light cycle is initiated. | Flower production is initiated when plants are taken from vegetative growth at 24-hour light and switched to 12 hours of light followed by 12 hours of dark during what would be the nocturnal period. Flowers mature typically 75 days after the flowering light cycle is initiated. |
| Proportion of hermaphrodite plants | 10% on average | None |
| Hardiness of plant | Tolerant to heat, cold, (USDA hardiness zone 4-11) *Pososphaera macularis* (powdery mildew), mold, pests and can thrive in different soil conditions. Because of long internodes and prominent stalk, may require more water than mother to maintain turgor in stems. | Tolerant to *Pososphaera macularis* (powdery mildew), mold and pests. Thrives in heat but is resistant to cold and humidity, resilience in many conditions wet or dry, hot or cold. |
| Breaking action | Above average, very sturdy. | Above Average, very sturdy. |
| Seed Shattering | Minimal | Minimal |
| Root rate after cutting/cloning | Has exhibited 100% success at new root development after cloning. Adventitious roots appear at 10-14 days. | Has exhibited 100% success at new root development after cloning. Adventitious roots appear at 10-14 days. |
| Total THC and CBD Content at harvest maturity | Total CBD content: 13%<br>Total THC content: 0.6%<br>Total CBD:THC Ratio: 22:1 | Total CBD content: 14%<br>Total THC content: 0.7%<br>Total CBD:THC Ratio: 20:1 |
| Total CBG content at harvest maturity | Total CBG: 1.1%<br>CBD:CBG:THC Ratio: 22:2:1 | Total CBG: 0.62%<br>CBD:CBG:THC Ratio: 20:1:1 |

The botanical descriptions provided are generalizing from plants grown indoors in controlled conditions. Total potential cannabinoid content is measured using a formula to account for decarboxylation of the acidic forms to allow for more accurate estimation. The formulas used are provided for convenience:

Total THC=THC+(THCA*(0.877));

Total CBD=CBD+(CBDA*(0.877));

Total CBG=CBG+(CBGA*(0.877)).

The W father has alternate, palmately compound leaves with 3-7 incredibly long and slender leaflets. Each leaflet has a length to width ratio of about 8:1 compared to '3 Crop' with about 5 or 6:1. Additionally, the W has serrated margins with significantly fewer teeth of about 23-30 compared to 33-43 on 3 Crop. The leaves on '3 Crop' resemble the mother more than the father, but the larger than average internodal spacing on the W father is exhibited in '3 Crop', though it is still more significant. Additionally, the W father was selected for its unusually high CBG levels which is a novel cannabinoid that is usually only seen in young growth or in small quantities at maturity because it is the precursor to some other cannabinoids such as THC, CBD, and CBC. '3 Crop' also has a higher than average CBG level (above 1%) which it most likely inherited from the W father. The W father also exhibits hermaphrodite tendencies when stressed and sometimes even naturally.

When compared to the U mother, '3 Crop' is generally significantly taller and more resilient. '3 Crop' has rapid growth in the vegetative state and will produce long, sturdy stalks and stems that will grow taller to out compete surrounding plants for light. The U mother on the other hand generally is shorter and wider growth but still has a similar leaf structure resembling the '3 Crop' but with shorter internodes. Additionally, the '3 Crop' exhibits much more prominent branching both from the stalk and 3° from branching off the stems. The U mother has fewer leaflets compared to the '3 Crop' with generally more serrations on the leaflet margins. The '3 Crop' has generally larger leaves than what is seen on the U mother, but the ratios of length:width both are about 5 or 6:1. Both plants produce impressive flower, but the U mother has spherical flowers whereas the '3 Crop' produces more conical flowers. The differences also go beyond just the appearance. The U mother prefers a hot climate and can tolerate more drought conditions. The '3 Crop', on the other hand, drinks more water, likely due to its rapid and intense growth, and needs more water to maintain the turgor pressure in the long stems to keep the plant upright. The U mother also grows more robustly when grown outdoors and not confined to a pot and will get about as wide as it gets tall. The '3 Crop' thrives in both indoor and outdoor conditions. Indoors it can be restricted in size because of the pot, however it will still grow substantially taller than what is expected of a root-bound plant and will outcompete surrounding plants for the light. Outdoors that growth is exponential and will grow significantly taller than wide because of its fibrous stalks.

When compared to another *Cannabis sativa* Hemp variety, 'CW24' (U.S. Plant Pat. No. 33,138), the '3 Crop' grows significantly taller with larger internodes. These prominent internodes and long sturdy stalks allow '3 Crop' to be used for fiber and will tower above other surrounding strains, such as 'CW24'. The 'CW24' leaflets are often more narrow than '3 Crop' and have significantly fewer serrations: 19-29 on 'CW24' compared to 33-43 on '3 Crop'. The 'CW24' flowers are grown closer together due to the shorter internodes which allow the flowers to grow more congested or overlapping throughout the plant while '3 Crop' only begins to have more congested flowers at the apical ends of branches. Additionally, the 'CW24' flower is a more compressed oval shape while the '3 Crop' is conical also accentuated by the long, prominent, string-like stigma that protrudes from each individual bud as compared to the shorter ones on 'CW24'. Along with its uniquely long and prominent stigma, '3 Crop' has a much more pronounced stipule on either side of a leaf or branch node that is almost two times larger than on 'CW24' at maturity. Mature '3 Crop' flowers have a sweet, fruity, bubble gum aroma while 'CW24' is more earthy and herbal. '3 Crop' has more CBG with 1% compared to non-detectable levels in 'CW24'. Also, '3 Crop' has a CBD:THC ratio of about 22:1 with CBD around 13% compared to 'CW24' of 26:1 with CBD only about 5-8%.

Growth Conditions:

Vegetative Growth Period: 24-hour light continuously. 78° F. and 60% humidity.

Flower Production Period: 12-hour light followed by 12-hour dark cycle repeating. 78° F. and 45% humidity.

Outdoor Growth:

'3 Crop' was grown outdoors on a farm in Sonoma County, Calif. The plants were planted as 30-day clones late in the season, Aug. 13, 2020, resulting in earlier flowering and smaller plants. The '3 Crop' plant has the potential to reach a maximum of 10 feet tall and 3 feet wide. Compared to indoor growth, the plant will be more robust and have a faster growth rate with wider leaves. When grown outdoors, the father, W, variety will reach 8 feet tall and 5 feet wide and the mother, U, variety will reach 8 feet tall and 6 feet wide.

Vigor:

Exhibits most vigorous and rapid growth during the vegetative state in which it grows strong, long stalks and stems that extend far upwards. Without maintenance, the plant will continue to grow upwards, noted to grow above our lights in our indoor facility which are set at 6 ft. Once flowering is induced, strong growth is still exhibited but focus switches from stalk development to formation of flowers and seeds. Vigor is exhibited in all conditions, but the focus of the growth will change depending on the plant cycle.

Coloration:

Changes in coloration occur with nutrient deficiencies or other variation in growing maintenance. The color of the leaves will not be consistent for the same plant grown in different conditions so cannot be the distinguishing feature of the plant.

The invention claimed is:

1. A new and distinct cultivar of hemp plant, named '3 Crop', as herein described and illustrated.

* * * * *